United States Patent [19]

Kiely

[11] Patent Number: 4,916,229

[45] Date of Patent: Apr. 10, 1990

[54] PYRIDINE CARBOXYLIC ACID DERIVATES

[75] Inventor: John S. Kiely, Ann Arbor, Mich.

[73] Assignee: Warner-Lambert Company, Morris Plains, N.J.

[21] Appl. No.: 237,247

[22] Filed: Aug. 26, 1988

Related U.S. Application Data

[62] Division of Ser. No. 78,618, Jul. 28, 1987, abandoned.

[51] Int. Cl.$^4$ .................... C07D 211/72; C07C 69/74
[52] U.S. Cl. .................................... 546/297; 560/124
[58] Field of Search ......................... 546/297; 560/124

[56] References Cited

FOREIGN PATENT DOCUMENTS 1409987 10/1975 United Kingdom ................ 546/297
2170804 1/1986 United Kingdom ................ 546/297

OTHER PUBLICATIONS

J. Chem. Soc., 1967; Organic Fluorine Compounds, Part XXXIX, Reactions of α-Fluoro-β-keto-esters.
Bulletin de la Societe Chimique de France, 1975; No. 212—Formyl fluoro cetones et esters, I. Preparation et derives acetyles.
Translation of Patent Application No. 1987—149,661, filed Jul. 22, 1987; Priority claimed 9/3/85, Japan, pub. Jul. 3, 1987.

*Primary Examiner*—Mary C. Lee
*Assistant Examiner*—Robert C. Whittenbaugh
*Attorney, Agent, or Firm*—Elizabeth M. Anderson

[57] ABSTRACT

The present invention covers a novel process for preparing substituted naphthyridines which are useful as intermediates in the production of certain antibacterial agents such as enoxacin. Also covered are novel intermediates in the process and methods for preparing them.

7 Claims, No Drawings

PYRIDINE CARBOXYLIC ACID DERIVATES

This is a division of Ser. No. 078,618 filed Jul. 28, 1987, now abandoned.

BACKGROUND OF THE INVENTION

The compounds prepared by the process of the present invention have been described in European application No. 187,376 as antibacterial agents.

British application No. 2,170,804 describes a process for producing 1-aryl-1,4-dihydro-4-oxo-1,8-naphthyridines and intermediates thereof as shown below.

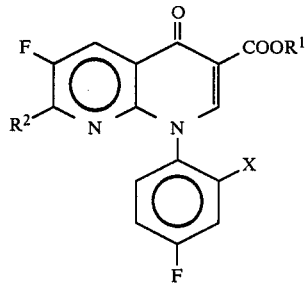

where
R¹ is hydrogen or carbonyl protecting group;
R² is halogen or an organic group attached via an O or N atom;
X is hydrogen or fluorine.
These are prepared from

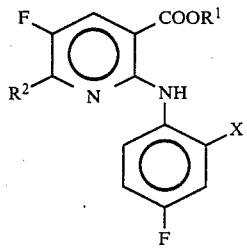

via an intermediate where COOR¹ is replaced by CO—CH₂COOR¹.

The compounds produced by the novel process of this invention are themselves intermediates for the known antibacterial agent enoxacin which is described in U.S. Pat. No. 4,359,578.

The chemical name of enoxacin is 1-ethyl-6-fluoro-1,4-dihydro-4-oxo-7-(1-piperazinyl)-1,8-naphthyridine-3-carboxylic acid.

The novel process of the present invention has the advantage of requiring fewer steps as it utilizes a more direct route than methods known in the art. Furthermore, the new process has industrial applications as it may be used to produce large quantities of the desired compounds. Certain of the intermediates of the present process are themselves novel compounds.

SUMMARY

The present invention is a process for producing compounds of formula I

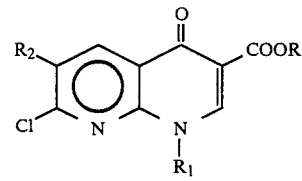

wherein R is hydrogen, a lower alkyl of from one to four carbon atoms or a cation; $R_1$ is lower alkyl of from one to four carbon atoms, cycloalkyl of from three to six carbon atoms or a substituted cycloalkyl; and $R_2$ is F, Cl, Br, or $CF_3$. The invention also covers novel intermediates to compounds of Formula I above.

DETAILED DESCRIPTION

The following schematic procedure illustrates the process of the present invention.

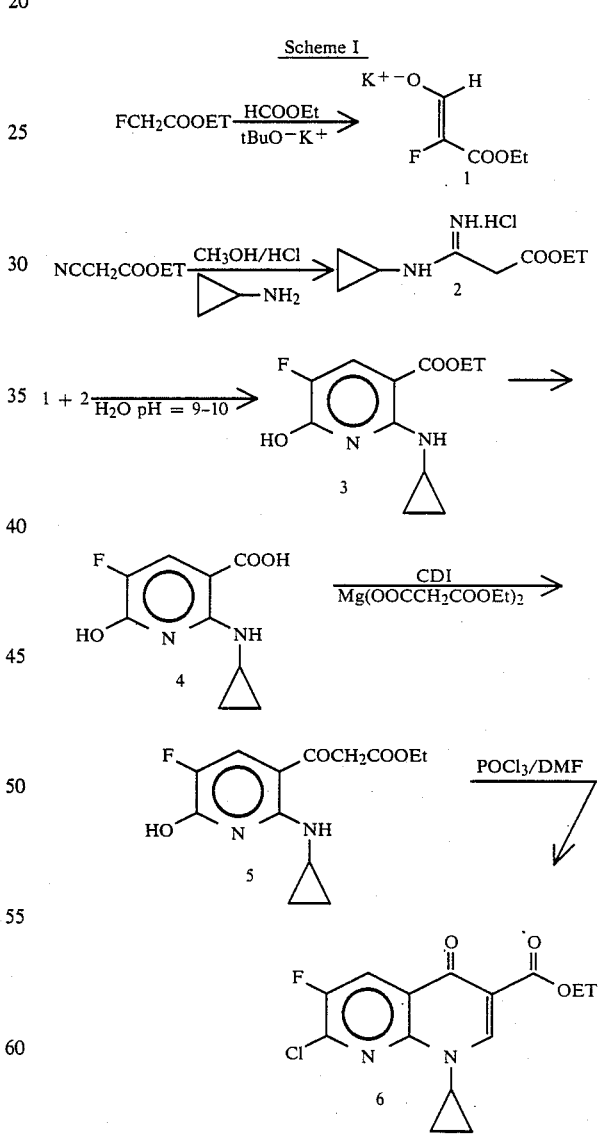

The alkali metal oxo-fluoropropanoic acid esters as exemplified in (1) above are prepared by reacting alkali metal alkoxide, alkylformate, and alkylhaloformate. The alkali metal alkoxide may be potassium, sodium, lithium, or cesium alkoxide wherein the alkoxide is a carbon group of from one to four carbon atoms. Preferably the alkali metal alkoxide is potassium-t-butoxide. The alkylformate is an alkyl of from one to four carbon atoms; preferably ethylformate is used. The alkylhaloacetate is a halogen such as fluorine, chlorine, or bromine; preferably ethylfluoroacetate is used. Alternatively an alkyl (3,3,3-trifluoropropanoate) is reacted in place of an alkylhaloacetate; preferably ethyl (3,3,3-trifluoropropanoate) is used.

Most preferred is the process wherein potassium-t-butoxide, ethylformate, and ethylfluoroacetate are used. The reaction temperature is from 0° to 55° C.; preferably from 10° to 15° C.

The 3-cyclopropylamino-3-imino propanoic acid ethyl ester hydrochloride as exemplified in (2) above, was prepared by reacting an alkyl ester of cyanoacetic acid with methanol and hydrochloric acid. The alkyl ester is methyl, ethyl or propyl. Preferably it is the ethyl ester.

The compounds of (1) and (2) above react together in a basic water or water/alcohol mixture solution to form the corresponding pyridine with a hydroxyl group on the ring as in (3) above. The reaction proceeds at a pH of from about 9 to 10 in water preferably or in a water/alcohol solution. The reaction proceeds for about one to three hours at a temperature of about 0° to 100° C., preferably at temperatures of about 20°–30° C. The ester portion of the pyridine is hydrolyzed to form the corresponding free acid as in (4) above. The hydrolysis preferably uses a strong inorganic acid such as $H_2SO_4$, $H_3PO_4$ or HBr, or HCl; preferably HCl is used. This compound is reacted with carbonyl diimidazole in an aprotic solvent, preferably tetrahydrofuran at from about 0° to 100° C. preferably at about 50°–70° for from about 1–24 hours. Preferably the reaction proceeds for from about three to five hours. This reaction solution is then reacted with an inorganic salt of malonic acid monoalkyl ester providing an oxo-ester pyridine, see compound 5 above. Preferably magnesium bis-(monoethylmalonate) is used. The process takes place at reflux in tetrahydrofuran for from one to twenty-four hours. Preferably the reaction time is for from 2 to 8 hours. This produces a compound as in (5) above.

A solution of phosphorus oxychloride and dimethylformamide is formed. The reaction temperature is from about 0° to about 15° C. Preferably it is from about −5° to +5° C. The compound as in (5) above is added to this solution to produce the desired compound of (6) above. The reaction time is from about 1 to about 12 hours. Preferably it is from about 2 hours to about 6 hours. The reaction occurs at a temperature of from about 25° to 100° C. Preferably the reaction temperature is from about 55° to about 60° C.

Compound 6 may be used directly in subsequent reactions or the ester function may be hydrolyzed to the free acid preferably in water or water alcohol mixture containing an inorganic acid, preferably HCl.

The compounds of formula VI may be converted, if desired, to a pharmaceutically acceptable acid addition or base salt thereof.

A preferred embodiment of the present invention is a process for the preparation of a compound of formula

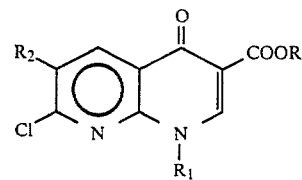

wherein R is hydrogen, a lower alkyl of from one to four carbon atoms, or a cation;

$R_1$ is a lower alkyl of from one to four carbon atoms, cycloalkyl of from three to six carbon atoms, or substituted cycloalkyl; and $R_2$ is F, Cl, Br, or $CF_3$; which comprises:

(a) reacting an alkali metal-oxo-halo- or trifluoromethyl- propanoic acid alkyl ester with 3-alkylamino-3-imino propanoic acid ester in a basic solution to form a compound of the formula

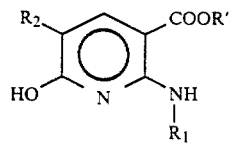

wherein $R_1$ is as described above and R' is alkyl;

(b) hydrolyzing the ester to form the corresponding free acid;

(c) reacting the free acid with carbonyldiimidazole and malonic acid monoalkyl ester to form a compound of the formula

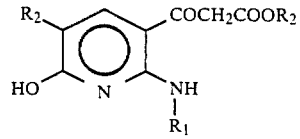

wherein $R_1$ and $R_2$ are as described above; and by known means producing a desired compound of formula I.

Preferred reaction conditions in step (a) above is a pH of from 9 to 10 in water or a water/alcohol mixture, 3-fluoropropanoic acid ethyl ester as a reactant, and temperatures of about 0° to 100° C. for from about one to three hours.

Preferred in step (b) above is using a strong inorganic acid such as HCl.

Preferred in step (c) above the malonic acid monoalkyl ester is magnesium bis-(monoalkylmalonate).

Further, a compound of formula I above may be reacted with an amine corresponding to a desired side chain of the formula:

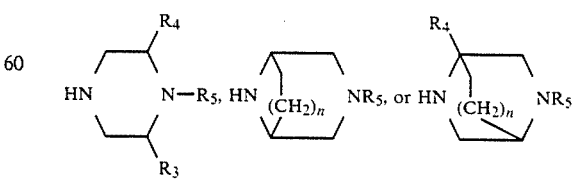

wherein $R_3$ and $R_4$ are each independently hydrogen or methyl;

$R_5$ is methyl, ethyl, or propyl; and n is 0, 1, or 2.

If desired, R₅ may be a protecting group which renders this site inert to the reaction conditions. Such protecting groups as the following may be utilized: acyl groups such as formyl, acetyl, trifluoroacetyl; alkoxycarbonyl groups such as ethoxycarbonyl, t-butoxycarbonyl, β,β,β-trichloroethoxycarbonyl, β-iodoethoxycarbonyl; aryloxycarbonyl groups such as benzyloxycarbonyl, p-methoxybenzyloxycarbonyl, phenoxycarbonyl; silyl groups such as trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction if desired, by procedures known to those skilled in the art. For example, the ethoxycarbonyl group may be removed by acid or base hydrolysis and the trityl group may be removed by hydrogenolysis or acid hydrolysis.

Or if desired a compound of formula I above may be reacted with an amine of the formula:

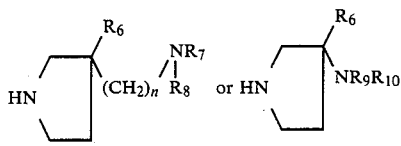

wherein n is 1 or 2; R₆ is hydrogen or an alkyl of from one to five carbon atoms or a cycloalkyl of from three to six carbon atoms; R₇ and R₈ are each independently hydrogen, an alkyl of from one to three carbon atoms, a cycloalky of from one to four carbon atoms or R₇ and R₈ may form a cyclic group of from three to five carbon atoms; R₉ and R₁₀ are each independently hydrogen, an alkyl of from one to three carbon atoms, or a cycloalkyl of from one to five carbon atoms, or a pharmaceutically acceptable acid addition or base salt thereof.

The compounds as exemplified as in (2), (3), (4) and (5) above in Scheme I are preferably for (2):

3-(cyclopropylamino)-3-imino propanoic acid ethyl ester monohydrochloride,
3-(cyclopropylamino)-3-imino propanoic acid methyl ester monohydrochloride,
3-(cyclopropylamino)-3-imino propanoic acid propyl ester monohydrochloride,
3-(cyclopropylamino)-3-imino propanoic acid n-butyl ester monohydrochloride,
3-(cyclobutylamino)-3-imino propanoic acid methyl ester monohydrochloride,
3-(cyclobutylamino)-3-imino propanoic acid ethyl ester monohydrochloride,
3-(cyclobutylamino)-3-imino propanoic acid propyl ester monohydrochloride,
3-(cyclobutylamino)-3-imino propanoic acid n-butyl ester monohydrochloride,
3-(ethylamino)-3-imino propanoic acid methyl ester monohydrochloride,
3-(ethylamino)-3-imino propanoic acid ethyl ester monohydrochloride,
3-(ethylamino)-3-imino propanoic acid propyl ester monohydrochloride,
3-(ethylamino)-3-imino propanoic acid n-butyl ester monohydrochloride,
3-(methylamino)-3-imino propanoic acid methyl ester monohydrochloride,
3-(methylamino)-3-imino propanoic acid ethyl ester monohydrochloride,
3-(methylamino)-3-imino propanoic acid propyl ester monohydrochloride,
3-(methylamino)-3-imino propanoic acid n-butyl ester monohydrochloride,
3-(propylamino)-3-imino propanoic acid methyl ester monohydrochloride,
3-(propylamino)-3-imino propanoic acid ethyl ester monohydrochloride,
3-(propylamino)-3-imino propanoic acid propyl ester monohydrochloride,
3-(propylamino)-3-imino propanoic acid n-butyl ester monohydrochloride; for (3):
2-(cyclopropylamino)-5-fluoro-6-hydroxy-3-pyridinecarboxylic acid ethyl ester,
2-(cyclopropylamino)-5-fluoro-6-hydroxy-3-pyridinecarboxylic acid n-butyl ester,
2-(cyclopropylamino)-5-chloro-6-hydroxy-3-pyridinecarboxylic acid n-butyl ester,
2-(cyclopropylamino)-5-bromo-6-hydroxy-3-pyridinecarboxylic acid n-butyl ester,
2-(cyclopropylamino)-5-trifluoromethyl-6-hydroxy-3-pyridinecarboxylic acid n-butyl ester,
2-(ethylamino)-5-fluoro-6-hydroxy-3-pyridinecarboxylic acid n-butyl ester,
2-(ethylamino)-5-chloro-6-hydroxy-3-pyridinecarboxylic acid n-butyl ester,
2-(ethylamino)-5-bromo-6-hydroxy-3-pyridinecarboxylic acid n-butyl ester,
2-(ethylamino)-5-trifluoromethyl-6-hydroxy-3-pyridinecarboxylic acid n-butyl ester,
2-(cyclobutylamino)-5-fluoro-6-hydroxy-3-pyridinecarboxylic acid n-butyl ester,
2-(cyclobutylamino)-5-chloro-6-hydroxy-3-pyridinecarboxylic acid n-butyl ester,
2-(cyclobutylamino)-5-bromo-6-hydroxy-3-pyridinecarboxylic acid n-butyl ester,
2-(cyclobutylamino)-5-trifluoromethyl-6-hydroxy-3-pyridinecarboxylic acid n-butyl ester,
2-(methylamino)-5-fluoro-6-hydroxy-3-pyridinecarboxylic acid n-butyl ester,
2-(methylamino)-5-chloro-6-hydroxy-3-pyridinecarboxylic acid n-butyl ester,
2-(methylamino)-5-bromo-6-hydroxy-3-pyridinecarboxylic acid n-butyl ester,
2-(methylamino)-5-trifluoromethyl-6-hydroxy-3-pyridinecarboxylic acid n-butyl ester,
2-(propylamino)-5-fluoro-6-hydroxy-3-pyridinecarboxylic acid n-butyl ester,
2-(propylamino)-5-chloro-6-hydroxy-3-pyridinecarboxylic acid n-butyl ester,
2-(propylamino)-5-bromo-6-hydroxy-3-pyridinecarboxylic acid n-butyl ester,
2-(propylamino)-5-trifluoromethyl-6-hydroxy-3-pyridinecarboxylic acid n-butyl ester,
2-(cyclopropylamino)-5-fluoro-6-hydroxy-3-pyridinecarboxylic acid propyl ester,
2-(cyclopropylamino)-5-chloro-6-hydroxy-3-pyridinecarboxylic acid propyl ester,
2-(cyclopropylamino)-5-bromo-6-hydroxy-3-pyridinecarboxylic acid propyl ester,
2-(cyclopropylamino)-5-trifluoromethyl-6-hydroxy-3-pyridinecarboxylic acid propyl ester,
2-(ethylamino)-5-fluoro-6-hydroxy-3-pyridinecarboxylic acid propyl ester,
2-(ethylamino)-5-chloro-6-hydroxy-3-pyridinecarboxylic acid propyl ester,
2-(ethylamino)-5-bromo-6-hydroxy-3-pyridinecarboxylic acid propyl ester, 2-(ethylamino)-5-trifluoromethyl-6-hydroxy-3-pyridinecarboxylic acid propyl ester,
2-(cyclobutylamino)-5-fluoro-6-hydroxy-3-pyridinecarboxylic acid propyl ester,
2-(cyclobutylamino)-5-chloro-6-hydroxy-3-pyridinecarboxylic acid propyl ester,
2-(cyclobutylamino)-5-bromo-6-hydroxy-3-pyridinecarboxylic acid propyl ester,
2-(cyclobutylamino)-5-trifluoromethyl-6-hydroxy-3-pyridinecarboxylic acid propyl ester,
2-(methylamino)-5-fluoro-6-hydroxy-3-pyridinecarboxylic acid propyl ester,
2-(methylamino)-5-chloro-6-hydroxy-3-pyridinecarboxylic acid propyl ester,
2-(methylamino)-5-bromo-6-hydroxy-3-pyridinecarboxylic acid propyl ester,
2-(methylamino)-5-trifluoromethyl-6-hydroxy-3-pyridinecarboxylic acid propyl ester,
2-(propylamino)-5-fluoro-6-hydroxy-3-pyridinecarboxylic acid propyl ester,
2-(propylamino)-5-chloro-6-hydroxy-3-pyridinecarboxylic acid propyl ester,
2-(propylamino)-5-bromo-6-hydroxy-3-pyridinecarboxylic acid propyl ester,
2-(propylamino)-5-trifluoromethyl-6-hydroxy-3-pyridinecarboxylic acid propyl ester,
2-(cyclopropylamino)-5-chloro-6-hydroxy-3-pyridinecarboxylic acid ethyl ester,
2-(cyclopropylamino)-5-bromo-6-hydroxy-3-pyridinecarboxylic acid ethyl ester,
2-(cyclopropylamino)-5-trifluoromethyl-6-hydroxy-3-pyridinecarboxylic acid ethyl ester,
2-(ethylamino)-5-fluoro-6-hydroxy-3-pyridinecarboxylic acid ethyl ester,
2-(ethylamino)-5-chloro-6-hydroxy-3-pyridinecarboxylic acid ethyl ester,
2-(ethylamino)-5-bromo-6-hydroxy-3-pyridinecarboxylic acid ethyl ester,
2-(ethylamino)-5-trifluoromethyl-6-hydroxy-3-pyridinecarboxylic acid ethyl ester,
2-(cyclobutylamino)-5-fluoro-6-hydroxy-3-pyridinecarboxylic acid ethyl ester,
2-(cyclobutylamino)-5-chloro-6-hydroxy-3-pyridinecarboxylic acid ethyl ester,
2-(cyclobutylamino)-5-bromo-6-hydroxy-3-pyridinecarboxylic acid ethyl ester,
2-(cyclobutylamino)-5-trifluoromethyl-6-hydroxy-3-pyridinecarboxylic acid ethyl ester,
2-(methylamino)-5-fluoro-6-hydroxy-3-pyridinecarboxylic acid ethyl ester,
2-(methylamino)-5-chloro-6-hydroxy-3-pyridinecarboxylic acid ethyl ester,
2-(methylamino)-5-bromo-6-hydroxy-3-pyridinecarboxylic acid ethyl ester,
2-(methylamino)-5-trifluoromethyl-6-hydroxy-3-pyridinecarboxylic acid ethyl ester,
2-(propylamino)-5-fluoro-6-hydroxy-3-pyridinecarboxylic acid ethyl ester,
2-(propylamino)-5-chloro-6-hydroxy-3-pyridinecarboxylic acid ethyl ester,
2-(propylamino)-5-bromo-6-hydroxy-3-pyridinecarboxylic acid ethyl ester,
2-(propylamino)-5-trifluoromethyl-6-hydroxy-3-pyridinecarboxylic acid ethyl ester,
2-(cyclopropylamino)-5-fluoro-6-hydroxy-3-pyridinecarboxylic acid methyl ester,
2-(cyclopropylamino)-5-chloro-6-hydroxy-3-pyridinecarboxylic acid methyl ester,
2-(cyclopropylamino)-5-bromo-6-hydroxy-3-pyridinecarboxylic acid methyl ester,
2-(cyclopropylamino)-5-trifluoromethyl-6-hydroxy-3-pyridinecarboxylic acid methyl ester,
2-(ethylamino)-5-fluoro-6-hydroxy-3-pyridinecarboxylic acid methyl ester,
2-(ethylamino)-5-chloro-6-hydroxy-3-pyridinecarboxylic acid methyl ester,
2-(ethylamino)-5-bromo-6-hydroxy-3-pyridinecarboxylic acid methyl ester,
2-(ethylamino)-5-trifluoromethyl-6-hydroxy-3-pyridinecarboxylic acid methyl ester,
2-(cyclobutylamino)-5-fluoro-6-hydroxy-3-pyridinecarboxylic acid methyl ester,
2-(cyclobutylamino)-5-chloro-6-hydroxy-3-pyridinecarboxylic acid methyl ester,
2-(cyclobutylamino)-5-bromo-6-hydroxy-3-pyridinecarboxylic acid methyl ester,
2-(cyclobutylamino)-5-trifluoromethyl-6-hydroxy-3-pyridinecarboxylic acid methyl ester,
2-(methylamino)-5-fluoro-6-hydroxy-3-pyridinecarboxylic acid methyl ester,
2-(methylamino)-5-chloro-6-hydroxy-3-pyridinecarboxylic acid methyl ester,
2-(methylamino)-5-bromo-6-hydroxy-3-pyridinecarboxylic acid methyl ester,
2-(methylamino)-5-trifluoromethyl-6-hydroxy-3-pyridinecarboxylic acid methyl ester,
2-(propylamino)-5-fluoro-6-hydroxy-3-pyridinecarboxylic acid methyl ester,
2-(propylamino)-5-chloro-6-hydroxy-3-pyridinecarboxylic acid methyl ester,
2-(propylamino)-5-bromo-6-hydroxy-3-pyridinecarboxylic acid methyl ester,
2-(propylamino)-5-trifluoromethyl-6-hydroxy-3-pyridinecarboxylic acid methyl ester; for (4):
2-(cyclopropylamino)-5-fluoro-6-hydroxy-3-pyridinecarboxylic acid,
2-(cyclopropylamino)-5-chloro-6-hydroxy-3-pyridinecarboxylic acid,
2-(cyclopropylamino)-5-bromo-6-hydroxy-3-pyridinecarboxylic acid,
2-(cyclopropylamino)-5-trifluoromethyl-6-hydroxy-3-pyridinecarboxylic acid,
2-(ethylamino)-5-fluoro-6-hydroxy-3-pyridinecarboxylic acid,
2-(ethylamino)-5-chloro-6-hydroxy-3-pyridinecarboxylic acid,
2-(ethylamino)-5-bromo-6-hydroxy-3-pyridinecarboxylic acid,
2-(ethylamino)-5-trifluoromethyl-6-hydroxy-3-pyridinecarboxylic acid,
2-(cyclobutylamino)-5-fluoro-6-hydroxy-3-pyridinecarboxylic acid,
2-(cyclobutylamino)-5-chloro-6-hydroxy-3-pyridinecarboxylic acid,
2-(cyclobutylamino)-5-bromo-6-hydroxy-3-pyridinecarboxylic acid,
2-(cyclobutylamino)-5-trifluoromethyl-6-hydroxy-3-pyridinecarboxylic acid,
2-(methylamino)-5-fluoro-6-hydroxy-3-pyridinecarboxylic acid,
2-(methylamino)-5-chloro-6-hydroxy-3-pyridinecarboxylic acid,
2-(methylamino)-5-bromo-6-hydroxy-3-pyridinecarboxylic acid,
2-(methylamino)-5-trifluoromethyl-6-hydroxy-3-pyridinecarboxylic acid, 2-(propylamino)-5-fluoro-6-hydroxy-3-pyridinecarboxylic acid,
2-(propylamino)-5-chloro-6-hydroxy-3-pyridinecarboxylic acid,
2-(propylamino)-5-bromo-6-hydroxy-3-pyridinecarboxylic acid,
2-(propylamino)-5-trifluoromethyl-6-hydroxy-3-pyridinecarboxylic acid; and for (5):
2-(cyclopropylamino)-5-fluoro-6-hydroxy-β-oxo-3-pyridinepropanoic acid ethyl ester,
2-(cyclopropylamino)-5-fluoro-6-hydroxy-β-oxo-3-pyridinepropanoic acid tert-butyl ester,
2-(cyclopropylamino)-5-chloro-6-hydroxy-β-oxo-3-pyridinepropanoic acid tert-butyl ester,
2-(cyclopropylamino)-5-bromo-6-hydroxy-β-oxo-3-pyridinepropanoic acid tert-butyl ester,
2-(cyclopropylamino)-5-trifluoromethyl-6-hydroxy-β-oxo-3-pyridinepropanoic acid tert-butyl ester,
2-(ethylamino)-5-fluoro-6-hydroxy-β-oxo-3-pyridinepropanoic acid tert-butyl ester,
2-(ethylamino)-5-chloro-6-hydroxy-β-oxo-3-pyridinepropanoic acid tert-butyl ester,
2-(ethylamino)-5-bromo-6-hydroxy-β-oxo-3-pyridinepropanoic acid tert-butyl ester,
2-(ethylamino)-5-trifluoromethyl-6-hydroxy-β-oxo-3-pyridinepropanoic acid tert-butyl ester,
2-(cyclobutylamino)-5-fluoro-6-hydroxy-β-oxo-3-pyridinepropanoic acid tert-butyl ester,
2-(cyclobutylamino)-5-chloro-6-hydroxy-β-oxo-3-pyridinepropanoic acid tert-butyl ester,
2-(cyclobutylamino)-5-bromo-6-hydroxy-β-oxo-3-pyridinepropanoic acid tert-butyl ester,
2-(cyclobutylamino)-5-trifluoromethyl-6-hydroxy-β-oxo-3-pyridinepropanoic acid tert-butyl ester,
2-(methylamino)-5-fluoro-6-hydroxy-β-oxo-3-pyridinepropanoic acid tert-butyl ester,
2-(methylamino)-5-chloro-6-hydroxy-β-oxo-3-pyridinepropanoic acid tert-butyl ester,
2-(methylamino)-5-bromo-6-hydroxy-β-oxo-3-pyridinepropanoic acid tert-butyl ester,
2-(methylamino)-5-trifluoromethyl-6-hydroxy-β-oxo-3-pyridinepropanoic acid tert-butyl ester,
2-(propylamino)-5-fluoro-6-hydroxy-β-oxo-3-pyridinepropanoic acid tert-butyl ester,
2-(propylamino)-5-chloro-6-hydroxy-β-oxo-3-pyridinepropanoic acid tert-butyl ester,
2-(propylamino)-5-bromo-6-hydroxy-β-oxo-3-pyridinepropanoic acid tert-butyl ester,
2-(propylamino)-5-trifluoromethyl-6-hydroxy-β-oxo-3-pyridinepropanoic acid tert-butyl ester,
2-(cyclopropylamino)-5-fluoro-6-hydroxy-β-oxo-3-pyridinepropanoic acid propyl ester,
2-(cyclopropylamino)-5-chloro-6-hydroxy-β-oxo-3-pyridinepropanoic acid propyl ester,
2-(cyclopropylamino)-5-bromo-6-hydroxy-β-oxo-3-pyridinepropanoic acid propyl ester,
2-(cyclopropylamino)-5-trifluoromethyl-6-hydroxy-β-oxo-3-pyridinepropanoic acid propyl ester,
2-(ethylamino)-5-fluoro-6-hydroxy-β-oxo-3-pyridinepropanoic acid propyl ester,
2-(ethylamino)-5-chloro-6-hydroxy-β-oxo-3-pyridinepropanoic acid propyl ester,
2-(ethylamino)-5-bromo-6-hydroxy-β-oxo-3-pyridinepropanoic acid propyl ester,
2-(ethylamino)-5-trifluoromethyl-6-hydroxy-β-oxo-3-pyridinepropanoic acid propyl ester,
2-(cyclobutylamino)-5-fluoro-6-hydroxy-β-oxo-3-pyridinepropanoic acid propyl ester,
2-(cyclobutylamino)-5-chloro-6-hydroxy-β-oxo-3-pyridinepropanoic acid propyl ester,
2-(cyclobutylamino)-5-bromo-6-hydroxy-β-oxo-3-pyridinepropanoic acid propyl ester,
2-(cyclobutylamino)-5-trifluoromethyl-6-hydroxy-β-oxo-3-pyridinepropanoic acid propyl ester,
2-(methylamino)-5-fluoro-6-hydroxy-β-oxo-3-pyridinepropanoic acid propyl ester,
2-(methylamino)-5-chloro-6-hydroxy-β-oxo-3-pyridinepropanoic acid propyl ester,
2-(methylamino)-5-bromo-6-hydroxy-β-oxo-3-pyridinepropanoic acid propyl ester,
2-(methylamino)-5-trifluoromethyl-6-hydroxy-β-oxo-3-pyridinepropanoic acid propyl ester,
2-(propylamino)-5-fluoro-6-hydroxy-β-oxo-3-pyridinepropanoic acid propyl ester,
2-(propylamino)-5-chloro-6-hydroxy-β-oxo-3-pyridinepropanoic acid propyl ester,
2-(propylamino)-5-bromo-6-hydroxy-β-oxo-3-pyridinepropanoic acid propyl ester,
2-(propylamino)-5-trifluoromethyl-6-hydroxy-β-oxo-3-pyridinepropanoic acid propyl ester,
2-(cyclopropylamino)-5-chloro-6-hydroxy-β-oxo-3-pyridinepropanoic acid ethyl ester,
2-(cyclopropylamino)-5-bromo-6-hydroxy-β-oxo-3-pyridinepropanoic acid ethyl ester,
2-(cyclopropylamino)-5-trifluoromethyl-6-hydroxy-β-oxo-3-pyridinepropanoic acid ethyl ester,
2-(ethylamino)-5-fluoro-6-hydroxy-β-oxo-3-pyridinepropanoic acid ethyl ester,
2-(ethylamino)-5-chloro-6-hydroxy-β-oxo-3-pyridinepropanoic acid ethyl ester,
2-(ethylamino)-5-bromo-6-hydroxy-β-oxo-3-pyridinepropanoic acid ethyl ester,
2-(ethylamino)-5-trifluoromethyl-6-hydroxy-β-oxo-3-pyridinepropanoic acid ethyl ester,
2-(cyclobutylamino)-5-fluoro-6-hydroxy-β-oxo-3-pyridinepropanoic acid ethyl ester,
2-(cyclobutylamino)-5-chloro-6-hydroxy-β-oxo-3-pyridinepropanoic acid ethyl ester,
2-(cyclobutylamino)-5-bromo-6-hydroxy-β-oxo-3-pyridinepropanoic acid ethyl ester,
2-(cyclobutylamino)-5-trifluoromethyl-6-hydroxy-β-oxo-3-pyridinepropanoic acid ethyl ester,
2-(methylamino)-5-fluoro-6-hydroxy-β-oxo-3-pyridinepropanoic acid ethyl ester,
2-(methylamino)-5-chloro-6-hydroxy-β-oxo-3-pyridinepropanoic acid ethyl ester,
2-(methylamino)-5-bromo-6-hydroxy-β-oxo-3-pyridinepropanoic acid ethyl ester,
2-(methylamino)-5-trifluoromethyl-6-hydroxy-β-oxo-3-pyridinepropanoic acid ethyl ester,
2-(propylamino)-5-fluoro-6-hydroxy-β-oxo-3-pyridinepropanoic acid ethyl ester,
2-(propylamino)-5-chloro-6-hydroxy-β-oxo-3-pyridinepropanoic acid ethyl ester,
2-(propylamino)-5-bromo-6-hydroxy-β-oxo-3-pyridinepropanoic acid ethyl ester,
2-(propylamino)-5-trifluoromethyl-6-hydroxy-β-oxo-3-pyridinepropanoic acid ethyl ester,
2-(cyclopropylamino)-5-fluoro-6-hydroxy-β-oxo-3-pyridinepropanoic acid methyl ester,
2-(cyclopropylamino)-5-chloro-6-hdyroxy-β-oxo-3-pyridinepropanoic acid methyl ester,
2-(cyclopropylamino)-5-bromo-6-hydroxy-β-oxo-3-pyridinepropanoic acid methyl ester,
2-(cyclopropylamino)-5-trifluoromethyl-6-hydroxy-β-oxo-3-pyridinepropanoic acid methyl ester, 2-(ethylamino)-5-fluoro-6-hydroxy-β-oxo-3-pyridine-propanoic acid methyl ester,
2-(ethylamino)-5-chloro-6-hydroxy-β-oxo-3-pyridine-propanoic acid methyl ester,
2-(ethylamino)-5-bromo-6-hydroxy-β-oxo-3-pyridine-propanoic acid methyl ester,
2-(ethylamino)-5-trifluoromethyl-6-hydroxy-β-oxo-3-pyridinepropanoic acid methyl ester,
2-(cyclobutylamino)-5-fluoro-6-hdyroxy-β-oxo-3-pyridinepropanoic acid methyl ester,
2-(cyclobutylamino)-5-chloro-6-hydroxy-β-oxo-3-pyridinepropanoic acid methyl ester,
2-(cyclobutylamino)-5-bromo-6-hydroxy-β-oxo-3-pyridinepropanoic acid methyl ester,
2-(cyclobutylamino)-5-trifluoromethyl-6-hydroxy-β-oxo-3-pyridinepropanoic acid methyl ester,
2-(methylamino)-5-fluoro-6-hydroxy-β-oxo-3-pyridine-propanoic acid methyl ester,
2-(methylamino)-5-chloro-6-hydroxy-β-oxo-3-pyridine-propanoic acid methyl ester,
2-(methylamino)-5-bromo-6-hydroxy-β-oxo-3-pyridine-propanoic acid methyl ester,
2-(methylamino)-5-trifluoromethyl-6-hydroxy-β-oxo-3-pyridinepropanoic acid methyl ester,
2-(propylamino)-5-fluoro-6-hydroxy-β-oxo-3-pyridine-propanoic acid methyl ester,
2-(propylamino)-5-chloro-6-hydroxy-β-oxo-3-pyridine-propanoic acid methyl ester,
2-(propylamino)-5-bromo-6-hydroxy-β-oxo-3-pyridine-propanoic acid methyl ester, or
2-(propylamino)-5-trifluoromethyl-6-hydroxy-β-oxo-3-pyridinepropanoic acid methyl ester.

The compounds of formula I of the present invention display antibacterial activity when tested by the microtitration dilution method as described in Heifetz, et al, Antimicr. Agents and Chemoth., 6, 124 (1974), which is incorporated herein by reference. They are also useful intermediates for known antibacterial agents such as enoxacin.

The compounds of the process of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloride, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differed from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds formed by the process of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about four carbon atoms except when specifically stated to be greater than four carbon atoms. Representative of such groups are methyl, ethyl, propyl, isopropyl, butyl, tert-butyl, and the like.

The cycloalkyl groups contemplated by the invention comprise those having three to six carbon atoms such as cyclopropyl, cyclobutyl, cyclopentyl, and cyclohexyl. The cycloalkyls may be substituted by halogens, alkyls, amines, or hydroxy groups.

Certain compounds of the invention may exist in optically active forms. The pure D isomer, pure L isomer as well as mixtures thereof including the racemic mixtures, are contemplated by the invention. Additional asymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. The tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methylcellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methylcellulose, sodium carboxymethylcellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples are provided to enable one skilled in the art to practice the present invention. The examples are not intended to in any way limit the scope of the invention rather they are illustrative thereof.

EXAMPLE 1

3-Methoxy-3-imino propanoic acid ethyl ester hydrochloride

The procedure of P. Waring and D. J. Brown, Australian Journal of Chemistry, (1977) 30, 621 was used.

3-Cyclopropylamino-3-imino propanoic acid ethyl ester hydrochloride

To 13.3 g of 3-methoxy-3-imino propanoic acid ethyl ester hydrochloride in absolute ethanol was added 4.18 g of cyclopropylamine. The modest exotherm was controlled using a cold water bath and the reaction was stirred overnight. The ethanol was removed with rotary-evaporation to give a viscous oil. This oil was triturated with ethyl ether (1000 ml) to give a colorless solid. Yield=13.44 g.
Analysis: Found (calc'd):
C, 46.06 (46.49); H, 7.31 (7.31); N, 13.51 (13.56)

EXAMPLE 2

Potassium-3-oxo-2-fluoropropanoic acid ethyl ester

The procedure of E. Elkik and M. Imbeaux-Oudette, Bull. Soc. Chem. Fr. (1975) 1165 was modified as follows. Potassium-t-butoxide (23.5 g) was suspended in ether (500 ml) and the flask cooled with a cold water bath. To this suspension was added dropwise a mixture of 16.8 ml of ethylformate and 20.1 ml of ethylfluoroacetate dissolved in 50 ml of ether. During the addition the temperature was maintained at $\leq 15°$ C. After the addition was complete the reaction was stirred for an additional 10 minutes. The solid potassium-3-oxo-2-fluoropropanoic acid ethyl ester formed could be collected by filtration and used as a slightly damp solid. Reference; E. D. Bergmann, I. Shalak, I. Gruenwald, J. Chem. Soc. (C) (1967) 2206-7.

EXAMPLE 3

Ethyl-2-cyclopropylamino-5-fluoro-6-hydroxylnicotinate
(2-(cyclopropylamino)-5-fluoro-6-hydroxy-3-pyridinecarboxylic acid ethyl ester)

3-Cyclopropylamino-3-imino propanoic acid ethyl ester hydrochloride (10.3 g) was suspended in 100 ml of methylene chloride and 25 ml of 2N NaOH was added. The two phase solution was mixed vigorously until all the suspension had dissolved. The methylene chloride layer was separated and evaporated to an oil by rotary evaporation. This oil was suspended in 30 ml of $H_2O$ and added to a solution of 35 ml of $H_2O$ containing 1.0 ml of piperidine and 0.6 ml of acetic acid. To the 3-cyclopropylamino-3-imino propanoic acid ethyl ester suspension in the buffered water was added the potassium-3-oxo-2-fluoro propanoic acid ethyl ester prepared on a 0.05 molar scale. The pH of the reaction was adjusted to pH=10 with acetic acid. The reaction was stirred for 90 minutes and the pH=9.0-9.5 maintained by addition of base (NaOH) as necessary. The slightly pink solid suspended in the reaction was collected by filtration and washed with $H_2O$ and dried at $\approx 100$ mm Hg at 40° C. for 12 hours to give 2.0 g of ethyl-2-cyclopropylamino-5-fluoro-6-hydroxynicotinate.
Analysis: Found (calc'd)
$C_{11}H_8FN_2O_3 \cdot 0.2H_2O$ C, 54.19 (54.18); H, 5.36 (3.47); N, 11.45 (11.49); F, 7.66 (7.79).

EXAMPLE 4

2-Cyclopropylamino-5-fluoro-6-hydroxynicotinic acid
(2-(cyclopropylamino)-5-fluoro-6-hydroxy-3-pyridinecarboxylic acid)

To a solution of 95% ethanol (20 ml) and 2N NaOH/$H_2O$ (40 ml) was added 2.65 g of ethyl 2-cyclopropylamino-5-fluoro-6-hydroxynicotinate. The inital suspension was refluxed for a total of six hours, then cooled, and evaporated to a solid. The solid was dissolved in 30 ml of $H_2O$ and acidified to pH=1 with 2N HCl solution. The solid formed upon acidification was collected by filtration and washed with $H_2O$ to give the crude acid product. This product was triturated with hot 95% ethanol, filtered, and dried to give 1.65 g of a beige colored solid, 2-cyclopropyl-5-amino-6-hydroxynicotinic acid.
Analysis: Found (calc'd)
$C_9H_9FN_2O_3 \cdot 0.1H_2O$ C, 50.43 (50.51); H, 4.36 (4.33); N, 12.99 (13.09).

EXAMPLE 5

3-(3-(2-Cyclopropylamino-5-fluoro-6-hydroxy)-pyridinyl)-3-oxopropanoic acid ethyl ester 1.53 g of 2-cyclopropylamino-5-fluoro-6-hydroxynicotinic acid was added to a solution of 70 ml of THF containing 1.75 g of carbonyldiimidazole. The initial suspension was stirred overnight to give a clear solution. To the solution was added 6.18 g of magnesium bis-monoethylmalonate and the resulting suspension was refluxed for 4 hours. The reaction was cooled and evaporated to a solid. This solid was partitioned between ethyl acetate (200 ml) and 1N HCl (200 ml). The ethyl acetate layer was separated and washed successively with saturated NaCl solution and saturated potassium bicarbonate solution. The organic layer was dried (MgSO4), filtered, and rotary-evaporated to a solid. This solid was crystallized from boiling 95% ethanol to give 0.77 g of the title compound.

Analysis: Found (calc'd):
C, 55.57 (55.31); H, 5.38 (5.36); N, 9.84 (9.93).

EXAMPLE 6

Ethyl-7-chloro-6-fluoro-1-cyclopropyl-1,4-dihydro-4-oxo-1,8-naphthyridine-3-carboxylate Dimethylformamide (20 ml) was cooled to <5° C. with a ice/salt bath and 0.7 ml of phosphorus oxychloride was added dropwise to the cooled dimethylformamide. After 5 minutes, 0.7 g of 3-(3-(2-cyclopropylamino-5-fluoro-6-hydroxy)pyridinyl)-3-oxopropanoic acid ethyl ester was added to the dimethylformamide solution and the mixture stirred at room temperature for 1 hour. After 1 hour at room temperature, the reaction was heated to 55°-60° C. for 4 hours then cooled to room temperature. The dimethylformamide solution was poured into 300 ml of water (0°-2° C.). The yellow solid which was formed was collected by filtration and washed thoroughly with water. The yellow solid was dried at ≃100 mm Hg at 60° for 14 hours to give 0.25 g of the title compound.

Analysis: Found (calc'd)
C, 53.72 (54.11); H, 3.80 (3.89); N, 9.10 (9.02).

I claim:

1. A compound of the name 3-(cyclopropylamino)-3-imino propanoic acid ethyl ester, monohydrochloride.

2. A compound of the name 2-(cyclopropylamino)-5-fluoro-6-hydroxy-3-pyridinecarboxylic acid ethyl ester.

3. A compound of the name 2-(cyclopropylamino)-5-fluoro-6-hydroxy-3-pyridinecarboxylic acid.

4. A compound of the name 2-(cyclopropylamino)-5-fluoro-6-hydroxy-β-oxo-3-pyridinepropanoic acid ethyl ester.

5. A compound of the name 2-(ethylamino)-5-fluoro-6-hydroxy-3-pyridinecarboxylic acid ethyl ester.

6. A compound of the name 2-(ethylamino)-5-fluoro-6-hydroxy-3-pyridinecarboxylic acid.

7. A compound of the name 2-(ethylamino)-5-fluoro-6-hydroxy-β-oxo-3-pyridinepropanoic acid ethyl ester.

* * * * *